(12) United States Patent
Miyagi et al.

(10) Patent No.: US 7,662,092 B2
(45) Date of Patent: Feb. 16, 2010

(54) ENDOSCOPE DEVICE WITH ELECTRICALLY ACTUATED BENDING

(75) Inventors: Takayasu Miyagi, Hachioji (JP); Toshinari Maeda, Hachioji (JP); Keiichi Arai, Hachioji (JP); Yuichi Ikeda, Tama (JP)

(73) Assignee: Olympus Corporation, Tokyo (JP)

( * ) Notice: Subject to any disclaimer, the term of this patent is extended or adjusted under 35 U.S.C. 154(b) by 410 days.

(21) Appl. No.: 10/830,958

(22) Filed: Apr. 23, 2004

(65) Prior Publication Data

US 2004/0267093 A1 Dec. 30, 2004

(30) Foreign Application Priority Data

Apr. 25, 2003 (JP) ............................. 2003-122830

(51) Int. Cl.
*A61B 1/00* (2006.01)
(52) U.S. Cl. ...................................... 600/148; 600/146
(58) Field of Classification Search ......... 600/145–150, 600/152
See application file for complete search history.

(56) References Cited

U.S. PATENT DOCUMENTS

| 4,982,725 | A | * | 1/1991 | Hibino et al. | ............... | 600/117 |
| 5,658,238 | A | * | 8/1997 | Suzuki et al. | ............... | 600/150 |
| 5,976,074 | A | * | 11/1999 | Moriyama | ................... | 600/144 |
| 6,354,945 | B1 | * | 3/2002 | Furuki et al. | .................. | 463/38 |
| 6,638,213 | B2 | * | 10/2003 | Ogura et al. | ................ | 600/148 |
| 2001/0037051 | A1 | * | 11/2001 | Fujii et al. | ................... | 600/146 |
| 2003/0023142 | A1 | * | 1/2003 | Grabover et al. | ............ | 600/143 |
| 2004/0034279 | A1 | * | 2/2004 | Arai et al. | ................... | 600/152 |

FOREIGN PATENT DOCUMENTS

| JP | 58-148994 | 9/1983 |
| JP | 60-57821 | 4/1985 |
| JP | 5-228102 | 9/1993 |
| JP | 06-054795 | 3/1994 |
| JP | 6-63010 | 3/1994 |
| JP | 6-189897 | 7/1994 |
| JP | 6-304126 | 11/1994 |
| JP | 11-327676 | 11/1999 |

* cited by examiner

*Primary Examiner*—John P Leubecker
*Assistant Examiner*—Philip R Smith
(74) *Attorney, Agent, or Firm*—Scully, Scott, Murphy & Presser, P.C.

(57) ABSTRACT

An electric bending endoscope according to the present invention includes a bending portion arranged to an inserting portion, a bending driving mechanism which electrically bends the bending portion, an operation input member which instructs an operation to the bending driving mechanism so that the bending driving mechanism bends the bending portion, and a bending angle holding mechanism which holds the bending angle of the bending portion.

8 Claims, 9 Drawing Sheets

ENDOSCOPE DEVICE WITH ELECTRICALLY ACTUATED BENDING

This application claims benefits of Japanese Application No. 2003-122830 filed on Apr. 25, 2003, the contents of which are incorporated by this reference.

BACKGROUND OF THE INVENTION

1. Field of the Invention

The present invention relates to an electric bending endoscope which electrically bends a bending portion arranged to a distal-end portion of an inserting portion.

2. Description of the Related Art

Recently, an endoscope is widely used. Various curing treatments are performed by inserting an elongated inserting portion in the body cavity so as to observe the organ in the body cavity or by using a therapeutic instrument inserted in a channel dedicated to the therapeutic instrument as needed. In the industrial field, the endoscope observes and examines inner scratches and corrosion of a steam generator, a turbine, an engine and a chemical plant by inserting the elongated inserting portion.

The endoscope has a bending portion which is freely bendable connected to a proximal-end side of a distal-end portion of the elongated inserting portion. The endoscope receives an instruction as to the bending amount which corresponds to a bending direction or a bending speed of the bending portion, by inputting means for a bending operation such as a bending operation lever or a joystick device arranged to an operating portion. In the endoscope, a bending operation wire is mechanically stretched and contracted based on the bending amount inputted as the instruction so as to bend the bending portion.

The above-mentioned endoscope contains an electric bending driving system, that is, electric bending endoscope, in which a motor as bending driving means included in the endoscope is electrically rotation-controlled, the driving force of the motor contracts and stretches the bending operation wire, and the bending portion is bent.

For example, Japanese Unexamined Patent Application Publication No. 6-63010 discloses an endoscope, in which a pad arranged like a cross as bending operation input means performs the operation for instructing the bending. Further, Japanese Unexamined Patent Application Publication No. 6-304126 discloses a joystick or the like as the bending operation input means.

In the electric bending endoscope having the above-mentioned bending operation input means, in the case of an endoscope which is not electrically operated but performs the bending operation by manually rotating a bending operation knob, the bending operation does not need to be executed with large-force rotation and the operability is improved.

SUMMARY OF THE INVENTION

An electric bending endoscope according to the present invention includes a bending portion arranged to an inserting portion, a bending driving mechanism which electrically bends the bending portion, an operation input member which instructs an operation to the bending driving mechanism so that the bending driving mechanism bends the bending portion, and a bending angle holding mechanism which holds the bending angle of the bending portion.

DETAILED DESCRIPTION OF THE PREFERRED EMBODIMENTS

Hereinbelow, a description is given of embodiments of the present invention with reference to the drawings.

First Embodiment

Figure 1:
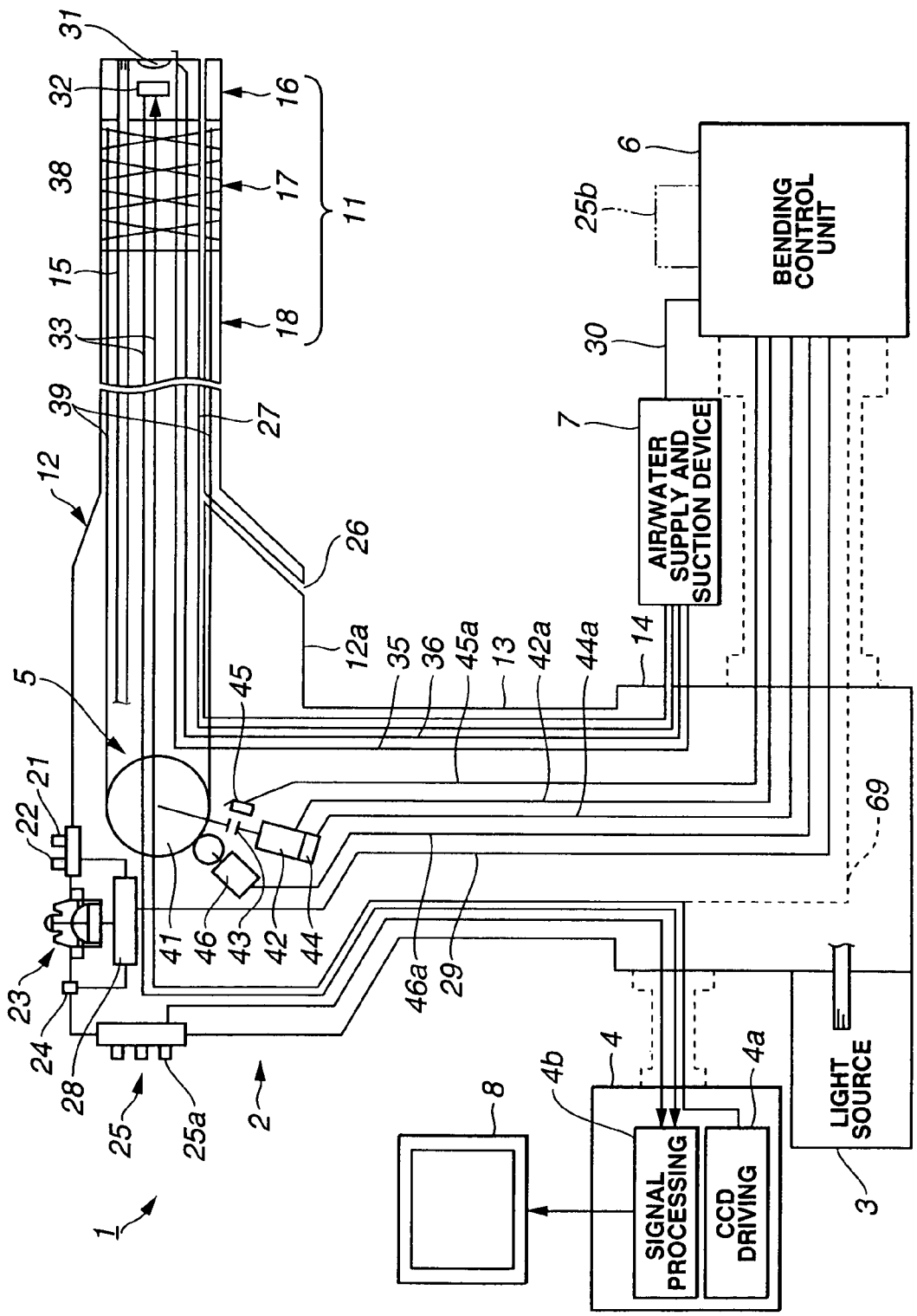
FIG. 1 is a diagram showing the entire structure of an electric bending endoscope apparatus according to a first embodiment of the present invention.
Figure 2:
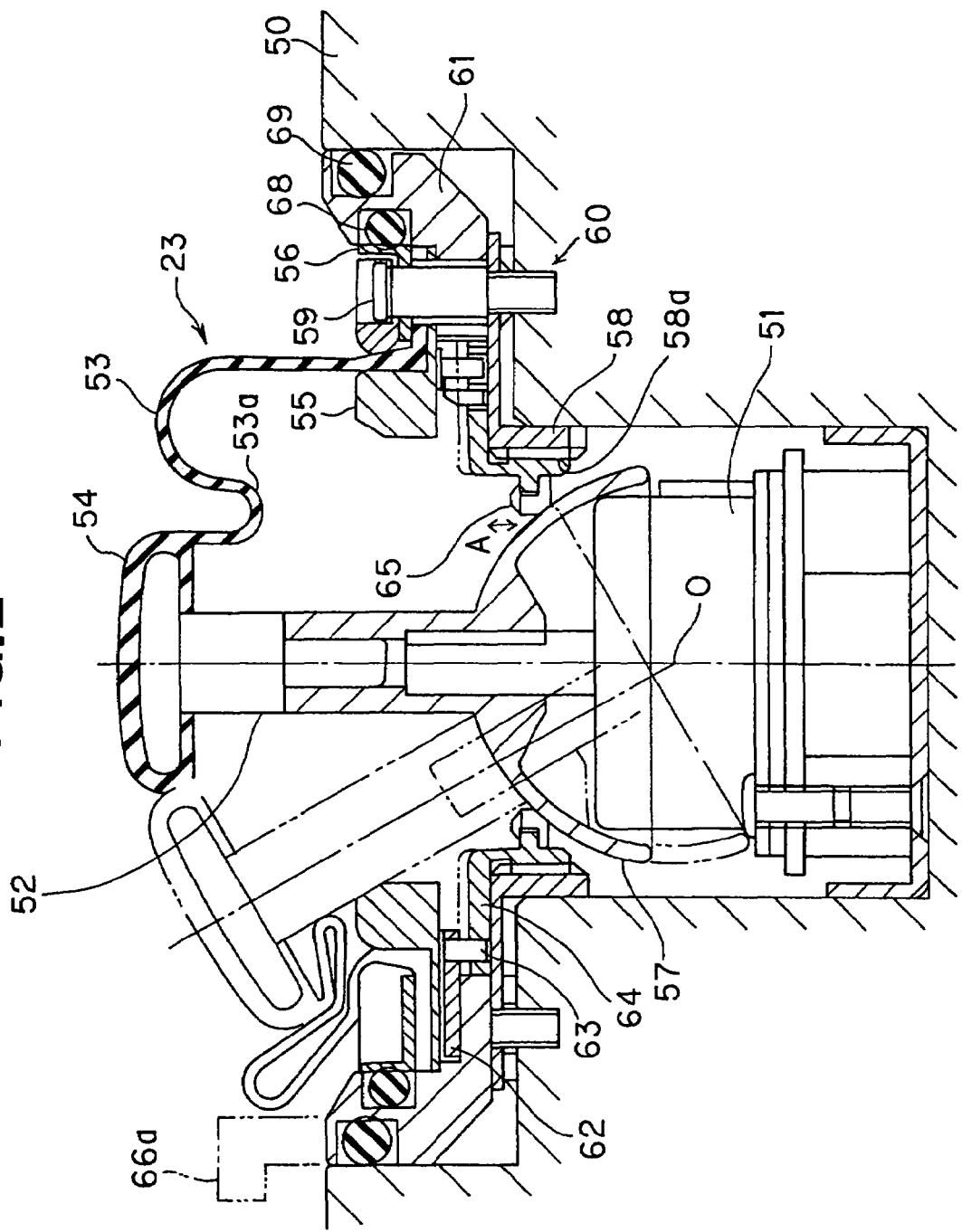
FIG. 2 is a sectional view showing a joystick device as bending operation input means.
Figure 3:
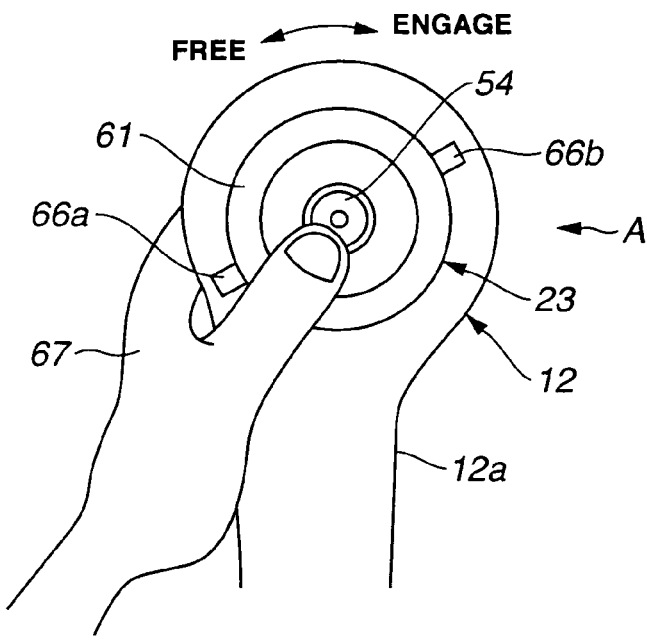
FIG. 3 is an explanatory diagram with respect to the schematic structure and also a using state of an operating portion according to a modification of the first embodiment.
Figure 4:
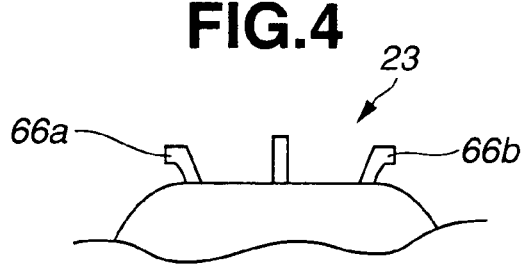
FIG. 4 is a view of the operating portion in view from an arrow A shown in FIG. 3.

FIGS. 1 to 4 show an electric bending endoscope according to a first embodiment of the present invention. FIG. 1 is an explanatory diagram with respect to the entire structure of the electric bending endoscope apparatus according to the first embodiment. FIG. 2 is a sectional view showing a joystick device as bending operation input means. FIG. 3 is an explanatory diagram with respect to the schematic structure and also a using state of a joystick device according to a modification of the first embodiment. FIG. 4 is a view of the joystick device in view from an arrow A shown in FIG. 3.

Referring to FIG. 1, an electric bending endoscope apparatus 1 comprises: an electric bending endoscope 2 having an electric bending function; a light source device 3 for supplying illumination light to the electric bending endoscope 2; a video processor, that is, a camera control unit (hereinafter, referred to as a CCU) 4 for performing signal processing for image pick-up means, which will be described later, incorporated in the electric bending endoscope 2; a bending control unit 6, as a bending control device, for controlling the driving operation of a bending driving unit 5 in the electric bending endoscope 2; an air/water supply and suction device 7 for controlling the supply and suction operation of the air/water; and a monitor 8 which displays a video signal outputted from the CCU 4.

The electric bending endoscope 2 comprises: an elongated inserting portion 11 inserted in the body cavity; an operating portion 12 which is continuously arranged to a proximal end of the inserting portion 11 and has a grip portion; and a universal code 13 extended from a side portion at the operating portion 12. A light guide cap in a connector 14 at the end portion of the universal cord 13 is connected to the light source device 3 and the illumination light is supplied to the light guide 15 from the light source device 3.

The inserting portion 11 comprises: a hard distal-end portion 16 arranged to the front end thereof; a bending portion 17 which is arranged to a back end of the distal-end portion 16 and is freely bent; and a flexible tube portion 18 which is long and flexible and is arranged to a back end of the bending portion 17.

The operating portion 12 comprises a grip portion 12a which is gripped by a user on the side of the inserting portion 11, that is, on the front end side of the operating portion 12. Arranged at the position on the back end side of the grip portion 12a, that is, at the position for easy operation of the gripping finger, an air/water supply button 21, a suction button 22, a joystick device 23 as the bending operation input means, and a clutch switch 24 for resetting, namely, disconnecting the transmission of driving force. Further, a scope switch 25 for performing instructions on video recording and the like to the CCU 4 is arranged at the position of the last end.

Furthermore, a therapeutic instrument inserting slit 26 for inserting a therapeutic instrument such as a biopsy clamp is arranged near the front end of the operating portion 12. The therapeutic instrument inserting slit 26 is communicated to a channel shared by the suction tube 27 therein.

The air/water supply button 21, suction button 22, joystick device 23, and clutch switch 24 are connected to an A/D substrate 28 for converting an analog signal into a digital signal. The A/D substrate 28 is connected to the bending control unit 6 via a signal line 29, and the bending control unit 6 is connected to the air/water supply and suction device 7 via a cable 30.

The illumination light from the light source device 3 is transmitted by the light guide 15, and the light is illuminated to an object side such as an affected part in the front direction of an illumination window arranged to the distal surface of the distal-end portion 16. An optical image of the illuminated object is formed by an objective lens 31 arranged to an observation window arranged adjacently to the illumination window. The object image is photoelectrically converted by a Charge-Coupled Device (hereinafter, referred to as a CCD) 32 as an image pick-up device arranged at the image forming position.

The CCD 32 is connected to the CCU 4 via a signal line 33 in which the inserting portion 11 is inserted and a signal line in a scope cable connected to the connector 14. A driving signal from a CCD driving circuit 4a in the CCU 4 is applied to the CCD 32, thereby inputting the photoelectrically converted image pick-up signal to the CCU 4. Further, the inputted signal is subjected to the signal processing by a signal processing circuit 4b and a video signal is generated. Then, the video signal is outputted to the monitor 8, and the image picked up by the CCD 32 is displayed on the display surface of the monitor 8 as an endoscope image.

The scope switch 25 arranged to the operating portion 12 has a plurality of switches. Switch functions such as a freeze (still image) instruction can be allocated to the switches. The switches are operated and then an instruction signal is inputted to the signal processing circuit 4b. Thus, the signal processing corresponding to the allocated function, e.g., the still image, is performed and outputted to the monitor 8.

An air supply tube 35 and a water supply tube 36 which supply the air and water to the surface of the objective lens 31, and the channel shared with the suction tube 27 are inserted in the inserting portion 11. The back ends of the air supply tube 35, the water supply tube 36, and the channel are connected to the air/water supply and suction device 7.

The air/water supply button 21 is operated. Then, the signal is inputted to the air/water supply and suction device 7 via the signal line 29, the bending control unit 6, and the cable 30. The air/water supply and suction device 7 supplies the air or water via the air supply tube 35 or the water supply tube 36. The suction button 22 is operated and, then, the air/water supply and suction device 7 sucks the air or water via the suction tube 27.

In the bending portion 17 arranged to the back end of the distal-end portion 16 in the inserting portion 11, a plurality of bending pieces 38 are rotatably connected in the longitudinal direction of the inserting portion 11. The bending piece 38 at the front end thereof is connected to the distal-end portion 16, and the bending piece 38 at the back end thereof is connected to the distal end of the flexible portion 18.

Two pairs of, that is, four bending operation wires (only one pair, namely, two wires are shown in the horizontal and vertical directions for the purpose of a brief description in FIG. 1) 39, 39 are inserted in the inserting portion 11 to bend the bending portion 17 in the vertical and horizontal directions of an observation field of view. The distal end of the bending operation wire 39 is strongly fixed to the bending piece 38 at the most distal end by wax at positions corresponding to the vertical and horizontal directions of the bending portion 17.

The bending portion 17 is bent in a desired direction by stretching the bending operation wires 39 in the direction corresponding to the desired direction and by contracting the bending operation wires 39, on the opposite direction thereof. The distal-end portion 16 on the front end of the bending portion 17 is positioned in a desired direction.

The bending operation wires 39, 39 are electrically stretched or contracted via the bending driving unit 5 arranged in the operating portion 12 by the amount corresponding to an inclining operation, that is, bending operation from the upright state of the joystick 52 (refer to FIG. 2) in the joy stick device 23 arranged to the operating portion 12, and the bending portion 17 is electrically bent.

That is, the inclining operation amount from the upright state using the joystick 52 in the joy stick device 23 constituting an operation input member is inputted to the bending control unit 6 as the input bending amount operation, namely, the instruction amount of the bending operation. The bending control unit 6 electrically drives the bending driving unit 5 arranged in the operating portion 12. The bending control unit 6 electrically bends the bending portion 17 by stretching and contracting the bending operation wires 39 at a bending angle corresponding to the input amount of the bending operation which is generated by electrically driving the bending driving unit 5 arranged in the operating portion 12. The bending driving unit 5 and the bending control unit 6 constitute a bending driving mechanism.

The bending driving unit 5 comprises: a sprocket 41 which winds and fixes the proximal-end portions of the pair of bending operation wires 39, 39 and stretches and contracts the pair of bending operation wires 39; a motor 42 which rotates the sprocket 41; an electromagnetic clutch 43 which is arranged between the sprocket 41 and the motor 42 and disconnects the driving force of the motor 42; a rotary encoder 44 which detects the rotating portion of the motor 42 as rotating position detecting means; and a clutch operation detecting switch 45 which detects the operation of the electromagnetic clutch 43.

The motor 42, the encoder 44, and the clutch detecting switch 45 are respectively connected to the bending control unit 6 via signal lines 42a, 44a, and 45a.

The bending driving unit 5 is connected to a potentiometer 46 for detecting the rotating position of the sprocket 41, as rotating position detecting means of the sprocket 41. The potentiometer 46 is connected to the bending control unit 6 via a signal line 46a, and outputs a rotating position signal indicating the detected rotating position of the sprocket 41.

The bending control unit 6 rotates the motor 42 based on the signals from the encoder 44 and the potentiometer 46 as the rotating position detecting means in accordance with a bending operation signal from the joy stick device 23 as the bending operation input means. Thus, the bending portion 17 is electrically bent.

According to the first embodiment, as will be described hereinbelow, the joystick device 23 as the bending operation input means comprises bending angle holding means which is held, namely, is locked at a desired bending angle and thus the operability is improved.

Next, a description is given of the structure of the joystick device 23 with reference to FIG. 2.

Referring to FIG. 2, a joystick main body 51 is attached to the bottom surface in a cylindrical concave portion arranged to a casing 50 of the operating portion 12 in the joystick device 23. The joystick 52 stands on the top surface of the joystick 51, as a bending operation instructing member which is freely inclined and inputs the instruction for the bending operation by the inclining operation.

The joystick main body 51 incorporates two potentiometers, for example, as electric signal generating means in the bending operation input means and a return-to-upright mechanism. In the two potentiometers, the resistance changes in accordance with the inclining direction of the joystick 52 by the inclining operation thereof. In the return-to-upright mechanism, the joystick 52 is returned to the upright state, that is, the position as the reference shown by a solid line shown in FIG. 2. Electric signals from the two potentiometers are inputted to the bending control unit 6 via the A/D substrate 28 shown in FIG. 1.

A waterproof operating surface 54 is formed by arranging a keycap to the upper end of the joystick 52 and by attaching the keycap to the center portion of a rubber cover 53 for covering it. In the rubber cover 53, a fold portion 53a is formed like a ring around the operating surface 54, then, the peripheral portion of the fold portion 53a is overlapped to a regulating member 55 which is substantially ring-shaped and regulates the inclining range of the joystick 52, and the peripheral portion is pressed in contact with the casing 50 by a screw 59 so as to be sandwiched by a pressing member 56 that is substantially ring-shaped.

The joystick 52 is covered with the rubber cover 53 to have a waterproof structure.

A member which is inverted to the down direction like an inverted cup, that is, a semispherical member is integrally arranged to the down end side of the joystick 52. The member is inclined with the joystick 52. A spherical portion 57 is formed to the outer circumferential surface thereof.

Referring to FIG. 2, the surface of the spherical portion 57 is on the spherical surface having the constant radius with respect to a central position O, as the center, of the inclination of the joystick 52. The position of the spherical surface does not change even if the joystick 52 is inclined.

A female screw portion 58a is formed to a short cylindrical portion, specifically, onto the inner circumferential surface on the side of the joystick 52 in the short cylindrical portion. A screw ring 58 having the female screw portion 58a is fixed to a part of the casing 50 on the outer circumferential side of the spherical portion 57. An engaging mechanism 60 has bending angle holding means on the top surface side of the screw ring 58. An engaging ring 61 constitutes the engaging mechanism 60 and is rotatably attached to the upper surface of the screw ring 58.

The engaging ring 61 constituting an engaging member is arranged to a step portion thereof, and is connected to a brake attaching member 64 having a male screw portion which is arranged to the outer circumferential surface of the short cylindrical portion and which is screwed to the screw ring 58 via a pin 63 projected to a relay ring 62 that rotates along with the engaging ring 61.

The brake attaching member 64 has a projected portion that is projected to the inner circumferential surface side of the short cylindrical portion of the screw ring 58, that is, on the joystick 52 side therein. A brake member 65 containing a member having a large friction coefficient such as rubber is attached to the projected portion.

The brake member 65 is screwed to the screw ring 58 and is attached to the brake attaching member 64 which is freely rotated along with the engaging ring 61. Therefore, the engaging ring 61 is rotated and then the brake member 65 is moved in the axial direction of the joystick 52 in association with the rotation, that is, is moved in the vertical direction as shown by reference symbol A. The engaging mechanism 60 is formed as the bending angle holding means using the friction force upon moving the brake member 65 in the down direction and pressing the brake member 65 in contact with the spherical portion 57. The engaging mechanism 60 can hold the joystick 52 to the inclining angle state or can release the holding by the friction force even if losing user's grip of the joystick 52.

That is, the engaging ring 61 is rotated and the brake member 65 is moved down in the axial direction of the joystick 52. Thus, the female screw portion 58a of the screw ring 58 and a screw pitch of the male screw portion are preset such that the brake member 65 changes from a state in which it is not in contact with the spherical portion 57 to a state in which it comes to strongly contact with the spherical portion 57.

The brake member 65 is in contact with the spherical portion 57. Then, as the contact area between the brake member 65 and the spherical portion 57 becomes wider, the friction force increases. Thus, the movement of the joystick 52 integrated to the spherical portion 57 is regulated. That is, when the joystick 52 is inclined and the bending portion 17 is bent, the force amount for the inclining operation is increased. When the user loses his grip of the joystick 52, the joystick 52 is set to be returned to the upright position. Further, the joystick 52 has a function for holding, namely, locking the joystick 52 to the inclining state in which the user loses his grip by the friction force to the spherical portion 57 caused by the brake member 65.

According to the first embodiment, the joystick 52 forming the bending operation input means is inclined for inputting the bending operation. The friction force caused by the brake member 65 suppresses the return to the upright position when the user loses his grip of the joystick 52. Consequently, the bending angle of the bending portion 17 is held to the state at the inclining angle.

An engaging lever 66a constituting an operating member rotates the engaging ring 61 for rotating operation. The engaging lever 66a is attached at one portion in the peripheral direction of the engaging ring 61, specifically, at the position for operation by the finger gripping the grip portion 12a, such that the engaging lever 66a is projected from the surface of the casing 50. Referring to FIG. 2, the engaging lever 66a is shown by a two-dotted line. The engaging lever 66a is also shown in the modification of the first embodiment in FIG. 3.

The joystick device 23 has a waterproof structure, namely, watertight structure by inserting O rings 68 and 69 to the inside and outside of the engaging ring 61.

The operation with the above-mentioned structure will be described according to the first embodiment.

Referring to FIG. 1, the electric bending endoscope 2 is connected to the light source device 3, CCU 4, and the bending control unit 6. The operator grips the grip portion 12a by, e.g., the left hand and has the inserting portion 11 by the right hand. The operator inserts the distal end of the inserting portion 11 in the body cavity from the mouth of the patient.

The illumination light from the CCU 4 is transmitted by the light guide 15, is outputted forward from the distal surface attached to the illuminating window of the distal-end portion 16, and illuminates the body cavity. The CCD 32 arranged at the image forming position of the objective lens 31 picks up the image of the illuminated body cavity. The image is displayed on the monitor 8 as the endoscope image.

The operator inclines the joystick 52 by operating the operating surface of the joystick device 23 with the finger on the gripping left hand so as to direct the inserting portion 11 along the luminal portion in the body cavity while observing the monitor 8.

The inclination of the joystick 52 changes the resistance of the potentiometer in the joystick device main body 51, and the resistance is converted into the digital signal via the A/D substrate 28. Further, the digital signal is transmitted to the bending control unit 6 as the signal for instructing the bending angle.

The bending control unit 6 applies a driving signal for rotating the motor 42 in the direction corresponding to the signal for instructing the bending angle. The rotation of the motor 42 rotates the sprocket 41, one of the bending operation wires 39, 39 is contracted and stretched, and the bending portion 17 is bent.

The bending angle as the bending amount is determined by the rotating angle of the sprocket 41, the rotating angle of the sprocket 41 is detected by the potentiometer 46, the detected signal, namely, the detected signal corresponding to the bending angle of the bending portion 17 is inputted to the bending control unit 6, and the rotation stops when the value of the detected signal matches the signal for instructing the bending angle.

That is, the operator inclines the joystick 52 in the bending direction and thus the bending driving unit 5 electrically contracts and stretches the bending operation wires 39, 39 at the instructed bending angle via the bending control unit 6. Consequently, the joystick 52 can easily be bent at the desired bending angle, as compared with the case of manually contracting and stretching the bending operation wires 39, 39.

As mentioned above, the inserting portion 11 can be inserted in the body cavity in the state in which the affected part or lesion portion as the observed target is observed. Upon setting the affected part or lesion portion to be observed, the bending portion 17 can be held, that is, locked to the bending state.

In this case, a mechanism for holding the bending angle is not arranged according to the conventional art. However, according to the first embodiment, the hand which grips the engaging lever 66a rotates the brake member 65 in the down direction. Thus, the brake member 65 is moved down and is in contact with the spherical portion 57 integrated to the joystick 52 (in the state shown in FIG. 2), and the joystick 52 can be held, that is, be locked, by the friction force in this case, to the state of the bending state and the bending portion 17 can be held to the state of the bending angle. The engaging lever 66a, the engaging ring 61, and the brake member 65 form the bending angle holding mechanism.

In the case of changing one bending angle to another one, the holding state of the bending angle is easily canceled by rotating the engaging lever 66a in the opposite direction, namely, in the direction for moving up the brake member 65.

As mentioned above, according to the first embodiment, when the joystick 52 is desired to be held at the desired bending angle, the bending portion 17 is held to the state of the bending angle by the operation for rotating the engaging lever 66a.

Thus, there is a merit that the operator is released from the operation for holding the bending state using the joystick 52 and concentrates on the operation of the treatment with the therapeutic instrument.

According to the conventional art, the joystick 52 must always be held to the state of inclining the joystick 52 so as to keep the predetermined bending angle and the operation is difficult for the treatment using the therapeutic instrument. However, according to the first embodiment, the bending angle is easily held and therefore another operation can easily be performed as well as the treatment using the therapeutic instrument.

Further, during the inserting operation, the bending angle is held and therefore the burden of the finger due to the bending operation is reduced. For example, when the burden of the finger which performs the bending operation upon insertion to the bent deep part side and the finger is to be free, the finger which performs the bending operation is detached from the operating surface and is free by holding the state of the bending angle with the operation of the engaging lever 66a.

As mentioned above, according to the first embodiment, it is possible to greatly facilitate the operation such as the treatment and observation using the endoscope and to excessively improve the operability or usability.

In the following description, the bending angle is held as one example. However, because of varying linearly, the dropping amount of the brake member 65 made by the engaging lever 66a, that is, the contact amount from the non-contact state to the state in which the brake member 65 is strongly held to the spherical portion 57, the friction resistance upon inclining operation, that is, the holding force amount is varied linearly. The inclining operation is set with the resistance desired by the operator.

Complementarily, by adjusting the dropping amount using the screw portion of the brake attaching member 64 which is screwed to the female screw portion 58*a* in the screw ring 58 and to which the brake member 65 is attached, the inclining operation of the joystick 52, namely, friction power thereof can controlled linearly. The operator can perform the inclining operation also in the state while setting the desired holding force.

That is, according to the conventional art, the operator can easily perform the joystick operation without his resistance until the instruction of the large bending angle. Therefore, the fine adjustment is difficult in many cases. However, according to the first embodiment, the operator can set the resistance to be operable one and can perform the operation. Further, the operator can easily execute the fine adjustment of the bending angle.

In particularly, in the case of bending operation using the gripping finger, the range of the inclining angle for inclining the joystick 52 by the finger becomes narrow because of ensuring the operability. The bending portion 17 needs to be bent at the actually wider angle by the angle of the joystick 52 within the narrow angle range. Therefore, with the easy fine adjustment, the operability of the bending will be greatly facilitated.

Next, a modification of the first embodiment will be described with reference to FIG. 3. FIG. 3 is a diagram for explaining with respect to the schematic structure of the operating portion and the using state, in which a schematic state of bending operation of the joystick device 23 by gripping the grip portion 12*a* of the operating portion 12 by the operator is explained. FIG. 4 is a view of the operating portion in view from an arrow A in FIG. 3. According to the modification, in order to easily hold the bending angle, engaging levers are arranged to a plurality of positions, as operating members in the bending angle holding means.

According to the first embodiment, the engaging lever 66*a* is arranged to the one portion on the engaging ring 61, serving as the position for facilitating the operation of the hand gripping the grip portion 12*a*. However, according to the modification, referring to FIGS. 3 and 4, in addition to the engaging lever 66*a*, a second engaging lever 66*b* is projected and arranged at the position facing the engaging lever 66*a*.

The other hand of a gripping left hand 67, namely, the right hand easily operates the second engaging lever 66*b*.

The engaging lever 66*a* arranged to the position for facilitating the operation is operated by the left hand 67 while operating the joystick device 23, thus to enable the bending and holding. Further, when the hand 67 is difficult to operate the joystick 23, the second engaging lever 66*b* at the position for easy operation of the right hand is operated so as to hold the bending angle.

According to the modification, it is possible to hold the bending angle, that is, to perform the engaging operation by both the right and left hands. The right and left hands can individually be used depending on the situation and thus the operability is improved.

Second Embodiment

Next, a second embodiment of the present invention will be described with reference to FIG. 1 too. According to the first embodiment, the bending angle is mechanically held. However, according to the second embodiment, the bending portion 17 is electrically held. Therefore, the joystick device according to the second embodiment may have the structure shown in FIG. 10, which will be described later, namely, may not have the engaging mechanism 60 including the brake member 65 and the like shown in FIG. 2.

Referring to FIG. 1, the operating portion 12 has the scope switch 25 comprising a plurality of switches. According to the second embodiment, an engaging switch 25*a*, one of the switches, is allowed to instruct the engaging operation.

The engaging switch 25*a* as an input member for instructing on holding the bending angle of the bending portion 17 is connected to the bending control unit 6 by a signal line 69 shown by a dotted line. Upon operating the engaging switch 25*a*, an instructing signal for holding the bending angle is transmitted to the bending control unit 6, and a CPU (not shown) for control of the bending control unit 6 does not receive (shuts out) the instructing signal which changes the bending angle from the joystick device 23 so as to hold the bending angle.

That is, the rotating state of the motor 42 for driving the bending just before operating the engaging switch 25*a* is held, that is, is locked by shutting out the instructing signal for changing the bending angle. Thus, the bending angle is held to the state.

According to the second embodiment, the bending angle of the bending portion 17 is held by one action for ON-operation of the engaging switch 25*a* and therefore the operation for holding the bending tube is excessively easy during locating the lesion portion at the operator's desired position upon the endoscope treatment or when the lesion portion is to be located at the desired position.

Further, the second embodiment has a merit that it can be applied to an existing electric bending endoscope having no holding means of the bending angle by simple modification.

In the above description, the engaging switch 25*a* for holding the bending angle is arranged to the electric bending endoscope 2. However, the engaging switch 25*b* may be arranged at a peripheral device to which the electric bending endoscope 2 is connected, e.g., a panel portion of the bending control unit 6 shown in FIG. 1 (shown by a two-dotted line in FIG. 1). Further, a foot switch (not shown) connected to the bending control unit 6 may have the function of the engaging switch 25*b*.

Upon arranging the engaging switch 25*b* to the panel portion of the bending control unit 6, there is a merit that the present invention can easily be applied to the existing electric bending endoscope.

Figure 5:
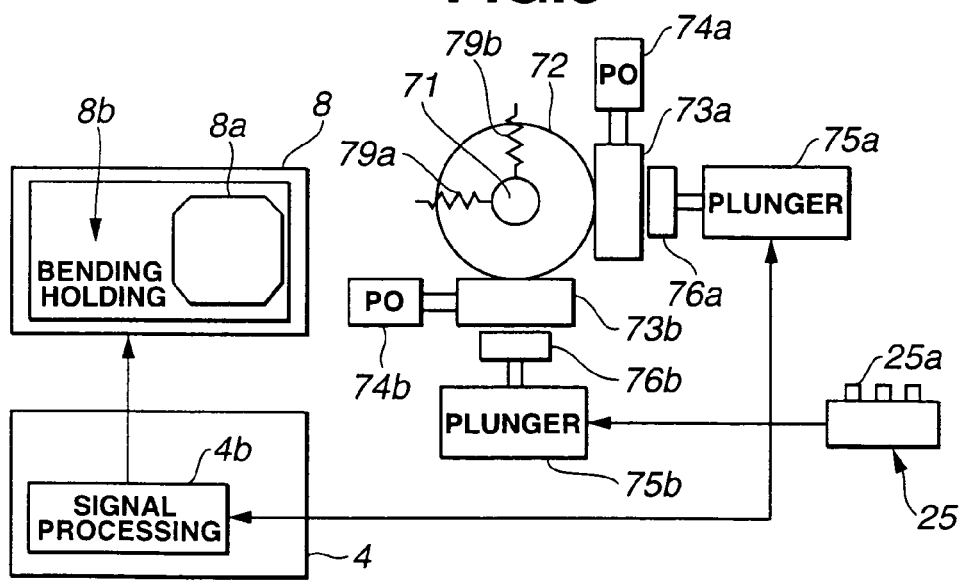
FIG. 5 is an explanatory diagram showing the structure of a peripheral portion in a joystick device according to a modification of the second embodiment of the present invention.

FIG. 5 is a diagram for explaining the structure near the proximal-end portion of the joystick in the joystick device according to the modification. According to the modification, too, the bending angle is electrically held. Further, according to the modification, the electric bending apparatus has means for notifying information on the holding of the bending angle as well as for holding the bending angle by the instructing signal for holding the bending angle, specifically, a notifying-by-display mechanism for displaying the holding of the bending angle on display means of the endoscope image.

The proximal end, namely, bottom end of a joystick 71 is connected to a freely rotatable ball 72. The ball 72 rotates in accordance with the direction for inclining the joystick 71 and thus the shafts of potentiometers (abbreviated to POs in FIG. 5) 74*a* and 74*b* are rotated via rotatable rollers 73*a* and 73*b* which are arranged to be in contact with the ball 72 in the perpendicular direction with respect to the spherical surface of the ball 72.

The resistance changes by rotating the shafts of the potentiometers 74*a* and 74*b*. That is, when the joystick 71 is inclined, the inclined direction and the inclining angle become input values for instructing the bending operation and are transmitted to the bending control unit 6. The bending control unit 6 controls the operation for bending the bending portion 17 at the bending angle corresponding to the instructing value. The joystick 71 is set to be returned to the upright state by springs 79a and 79b, as elastic members, which are mutually forced to the perpendicular directions.

According to the modification, brake members 76a and 76b are projected by plungers 75a and 75b comprising actuators such as aircylinders or thrust motors. The brake members 76a and 76b are arranged adjacently to the rollers 73a and 73b. For example, by operating the engaging switch 25a as one of the switches of the scope switch 25, the plungers 75a and 75b enter the operating state, and the brake members 76a and 76b are projected and are pressed in contact with the rollers 73a and 73b so as to prevent the rotation of the rollers 73a and 73b.

The holding means of the bending angle is formed such that, in this state, the rotation of the ball 72 is regulated and the joystick 71 is held to the state of the inclining angle just before operating the engaging switch 25a.

According to the modification, an operating signal of the engaging switch 25a is inputted to the signal processing circuit 4b in the CCU 4. The signal processing circuit 4b reads, from a ROM or the like arranged in the signal processing circuit 4b, information corresponding to the operating signal such as a character signal or characters for holding the bending angle, multiplexes the read data to a video signal, and outputs the multiplexed signal to the monitor 8. The signal processing circuit 4b and the monitor 8 form a notifying mechanism for notifying that the bending angle of the bending portion is held.

Indication 8b of "the bending is held", for example, is shown on a display area or the like adjacent to a display area 8a of the endoscope image in the display surface of the monitor 8.

According to the modification, the bending angle is held by one action for operating the engaging switch 25a.

Upon operation for holding the bending angle, the indication of the operation is displayed on the monitor 8 and therefore the operator easily grasps the state and the operability is improved. That is, the operator usually observes the monitor 8 for displaying the endoscope image, and upon holding the bending angle on the monitor 8, information on the holding of the bending angle is displayed. Thus, the state for holding the bending angle is confirmed by the operator in a state in which he views the endoscope image and the operability is improved.

Third Embodiment

Figure 6:
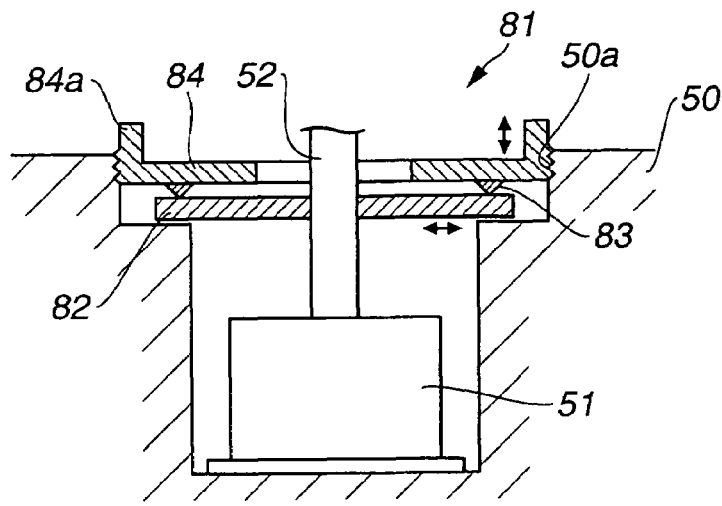
FIG. 6 is an explanatory diagram showing the schematic structure of a joystick device according to the third embodiment of the present invention according to the third embodiment of the present invention.

Next, a third embodiment of the present invention will be described with reference to FIG. 6. FIG. 6 is a diagram for explaining the schematic structure of a main portion of a joystick device 81 according to the third embodiment of the present invention. The third embodiment is another embodiment using the friction similarly to the first embodiment.

The joystick 52 stands on the joystick device main body 51 and is freely inclined. A disc 82 is freely slidable in the horizontal direction along the inclined direction caused by the inclining operation of the joystick 52. The disc 82 is attached to the joystick 52 in the halfway of the axial direction of the joystick 52. Further, an engaging ring 84 having a brake member 83 on the bottom surface is arranged to the upper side of the joystick 52, and the engaging ring 84 has a male screw portion which is screwed to the female screw portion 50a peripherally arranged on the casing 50.

An engaging lever 84a is attached to one portion or two portions of the engaging ring 84, and the brake member 83 is moved up and down in accordance with the rotating direction by rotating the engaging lever 84a.

By rotating the engaging lever 84a and moving down the engaging ring 84, the brake member 83 comes into contact with the disc 82 that operates interlockingly to the joystick 52. The disc 82 is held by the friction force, thereby holding the inclining state of the joystick 52. In this case, the holding force is variably set linearly.

Other structures are basically as same as those according to the first embodiment. The operation and advantages according to the third embodiment are basically the same as those according to the first embodiment.

Figure 7:
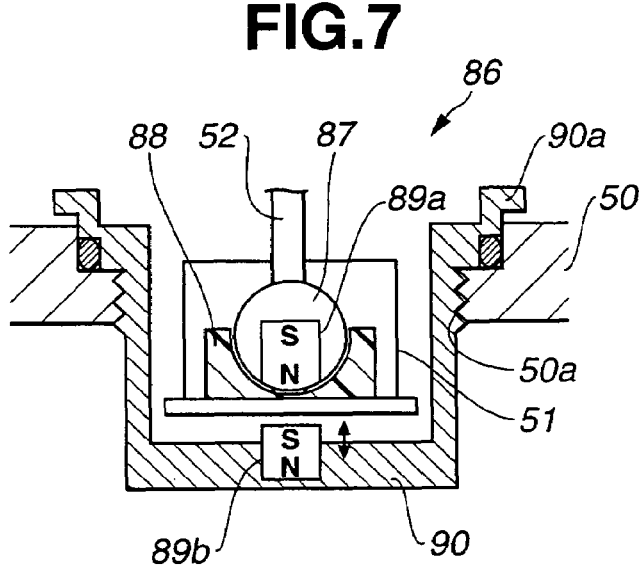
FIG. 7 is a diagram showing the schematic structure of a joystick device according to a first modification of the third embodiment.

FIG. 7 shows the schematic structure of a main portion of a joystick device 86 according to a first modification of the third embodiment, in which the bending angle is held by the magnetic force.

Referring to FIG. 7, the bottom end of the joystick 52 is connected to a ball 87 in the joystick device main body 51, and the ball 87 is freely rotatably held by a ball receiver 88. Further, the ball 87 rotates in accordance with the inclining operation of the joystick 52.

An magnet 89a is embedded to the bottom side of the ball 87 and an engaging frame 90 having a magnet 89b is rotatably arranged to the down direction of the magnet 89a.

The polarities of the two magnets 89a and 89b are arranged to have the opposite ones, and the suction magnetic force acts. The engaging frame 90 is screwed to a female screw portion 50a arranged to the casing 50, and the magnet 89b is moved up and down by rotating an engaging lever 90a projected from the casing 50.

The one magnet 89b is moved up and down, thereby changing the distance between the magnets 89a and 89b. Further, the magnetic force acting to the magnets 89a and 89b changes and therefore force for holding the inclining angle of the joystick 52 changes. Further, the joystick 52 is held by the contracting force when the distance is the shortest. In this case, too, the holding force can variably be set.

According to the first modification, because the friction is not used, the endurance is advantageous. Other structures and advantages are the same as those according to the first embodiment.

Figure 8:
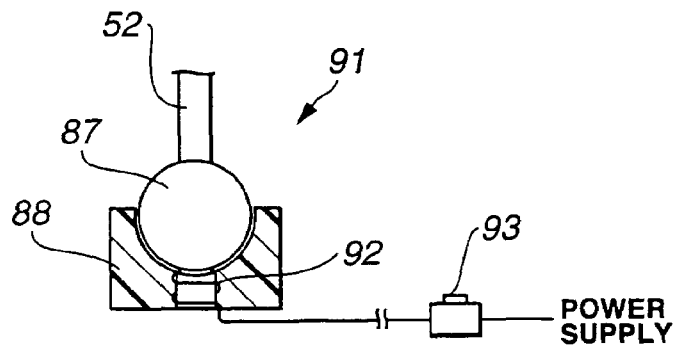
FIG. 8 is a diagram showing the schematic structure of a main portion of a joystick device according to a second modification of the third embodiment.

FIG. 8 is a diagram for explaining the schematic structure of a main portion of a joystick device 91 according to a second modification of the third embodiment. The joystick device 91 holds the bending angle by an electromagnet.

Referring to FIG. 8, the bottom end of the joystick 52 is attached to the ball 87, and the ball 87 is rotatably held by the ball receiver 88.

An electromagnet 92 is arranged to the ball receiver 88. Current is fed from a power supply for excitation from the bending control unit 6 by operating the engaging switch 93. The ball 87 contains a ferromagnetic material such as iron. The electromagnet 92 is excited, that is, is magnetized and then the ball 87 is sucked and held to the electromagnet 92, and the joystick 52 is held to the inclining angle in the state just before.

According to the second modification, the structure is simple because there is no mechanical movement and thus it is advantageous in easy assembling and the durability. Other structures and advantages are the same as those according to the first embodiment.

Figure 9:
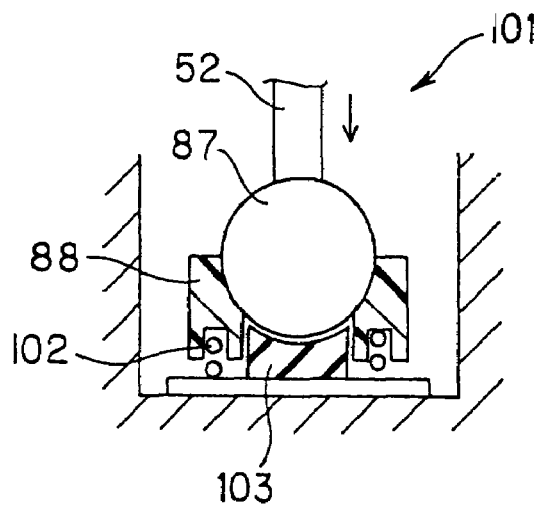
FIG. 9 is a diagram showing the schematic structure of a main portion of a joystick device according to a third modification of the third embodiment.

FIG. 9 is a diagram for explaining the schematic structure of a main portion of a joystick device 101 according to the third modification of the third embodiment. The joystick device 101 finely adjusts the bending operation by using the friction force.

Referring to FIG. 9, the ball 87 on the bottom end of the joystick 52 is freely rotatably held by the ball receiver 88 containing a Teflon (trademark) material including fluorocarbon resin having low friction-resistance, and the ball receiver 88 is forced up by a spring 102.

A hole is provided in the center of the ball receiver 88, and the ball receiver 88 further comprises a friction applying member 103 containing, for example, a rubber member having high friction-resistance. In the normal operating state, the spring 102 forces the ball receiver 88 in the upper direction and the ball 87 is freely rotated in contact with the ball receiver 88 having the low friction-resistance.

In this state, the bending operation is executed by inclining the joystick 52. In the case of fine adjustment of the bending operation, the joystick 52 is forcedly pressed to the down direction. Thus, the ball receiver 88 is moved down, the ball 87 comes into contact with the friction applying member 103 having the high friction-resistance, the resistance increases against the operation of the joystick 52, and the fine adjustment is easily performed.

With the above-mentioned structure, the operator can finely adjust the joystick by one action and the operability is improved.

Figure 10:
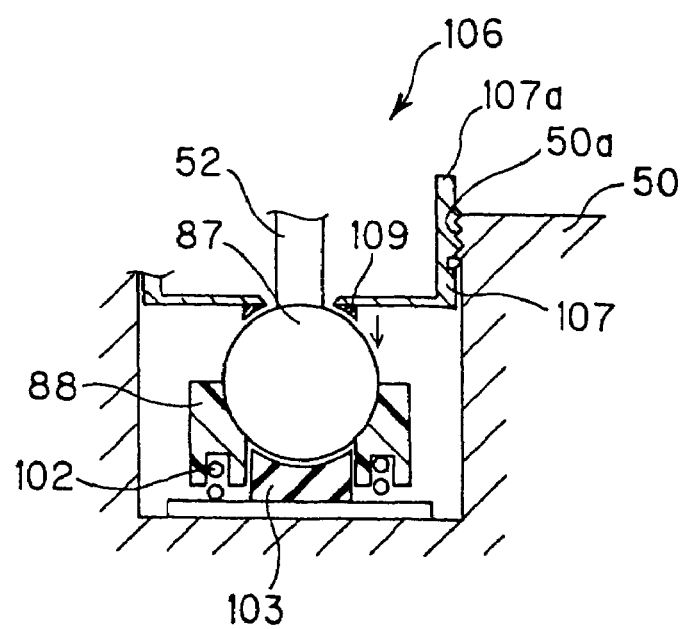
FIG. 10 is a diagram showing the schematic structure of a main portion of a joystick device according to a fourth modification of the third embodiment.

Incidentally, the structure of the joystick device 101 may be modified as shown in FIG. 10. A joystick device 106 shown in FIG. 10 has the structure shown in FIG. 9, and also has a pressing member 109 is attached to an engaging frame member 107 passing through the proximal end of the joystick 52 in a hollow portion thereof, facing the ball 87.

A male screw portion screwed to the female screw portion 50a arranged to the casing 50 is arranged around the engaging frame member 107. A lever 107a of the engaging frame member 107 is rotated, thus the engaging frame member 107 is moved down, and the ball 87 is pressed down via the pressing member 109 to be in contact with the friction applying member 103. Further, the inclining angle of the joystick 52 is held.

The operation and advantage in this case are the same as those according to the first embodiment.

According to the first to third embodiments, the joystick 52 is used for the inclining operation as the bending operation input means. However, the inclining operation can be achieved by rotating the ball such as a mouse or a trackball. Further, according to the second embodiment, the bending operation input means may be a cross pad or the like.

Fourth Embodiment

Next, a fourth embodiment of the present invention will be described with reference to FIGS. 11 and 12.

Figure 11:
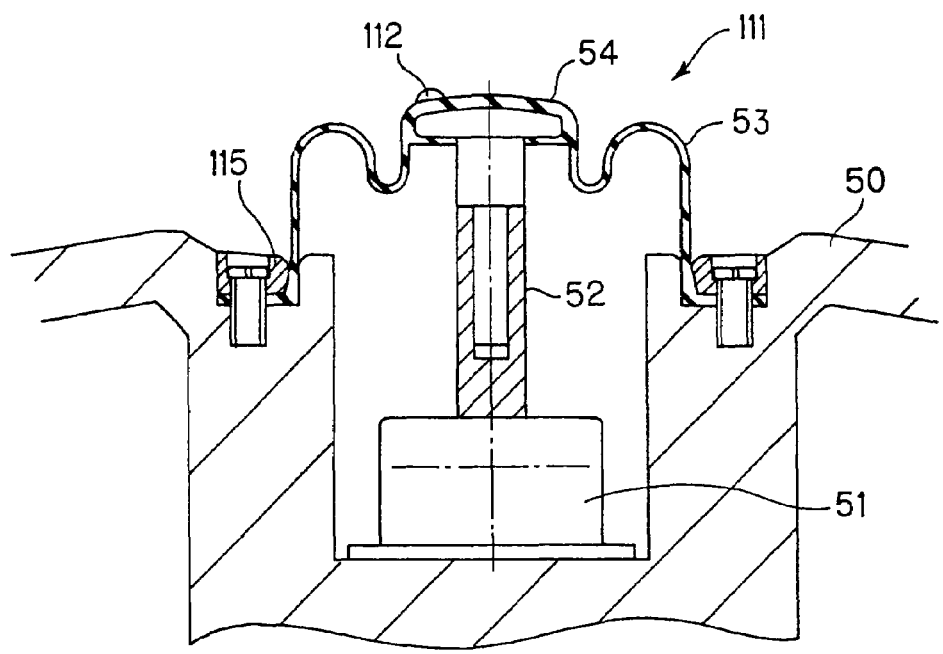
FIG. 11 is a sectional view showing the schematic structure of a joystick device according to the fourth embodiment of the present invention.

FIG. 11 is a sectional view showing the schematic structure of a joystick device according to the fourth embodiment of the present invention. FIG. 12 is a plan view showing the joystick device.

A joystick device 111 according to the fourth embodiment has the structure according to the second embodiment and has the operating surface 54 as a feature. That is, according to the fourth embodiment, the joystick device 111 comprises direction identifying means which identifies the operating direction by the tactile sense.

In the joystick device 111, the joystick 52 stands on the joystick device main body 51 arranged in a concave portion arranged to the casing 50, and a keycap is arranged to the top end of the joystick 52 and is covered with the rubber cover 53 to form the operating surface 54 with the waterproof structure.

The peripheral portion of the rubber cover 53 is fixed to the casing 50 at a fixing ring 115, with the watertight structure.

According to the fourth embodiment, the projection 112 is arranged at the position deviated on the operating surface 54 of the joystick 52 as the operating direction identifying means which can identify, that is, determine the operating direction by the tactile sense.

Figure 12:
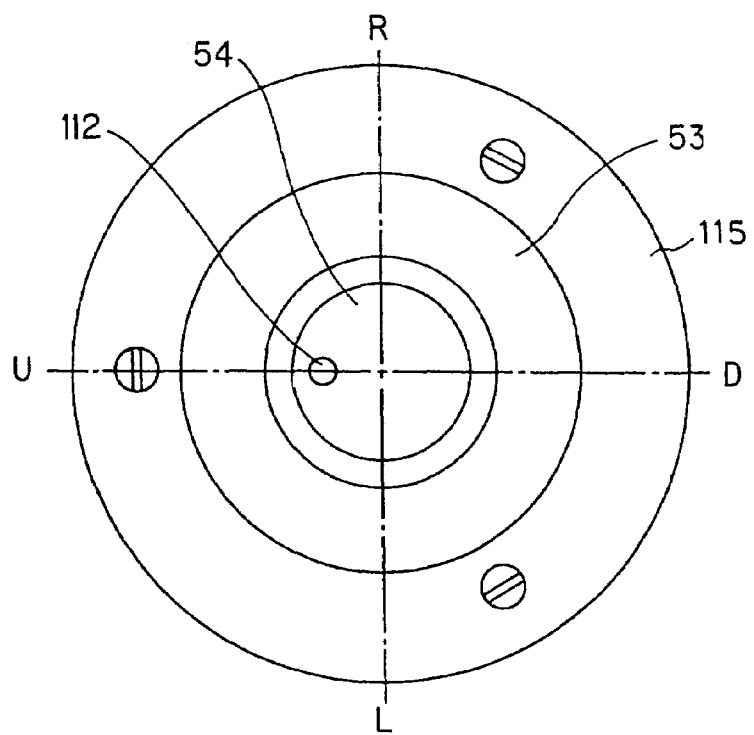
FIG. 12 is a plan view showing an operating surface of the joystick device according to the fourth embodiment.
Figure 13:
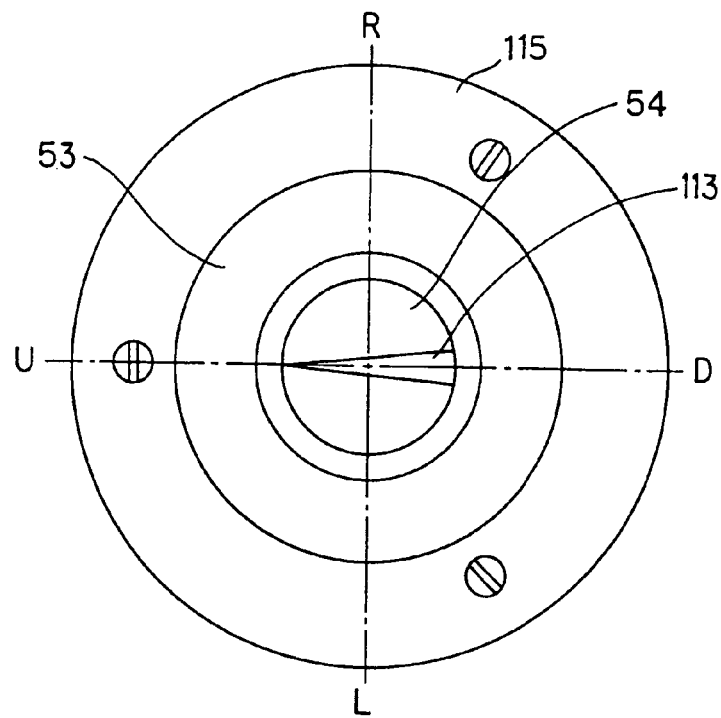
FIG. 13 is a plan view showing an operating surface of the joystick device according to a first modification of the fourth embodiment.
Figure 14:
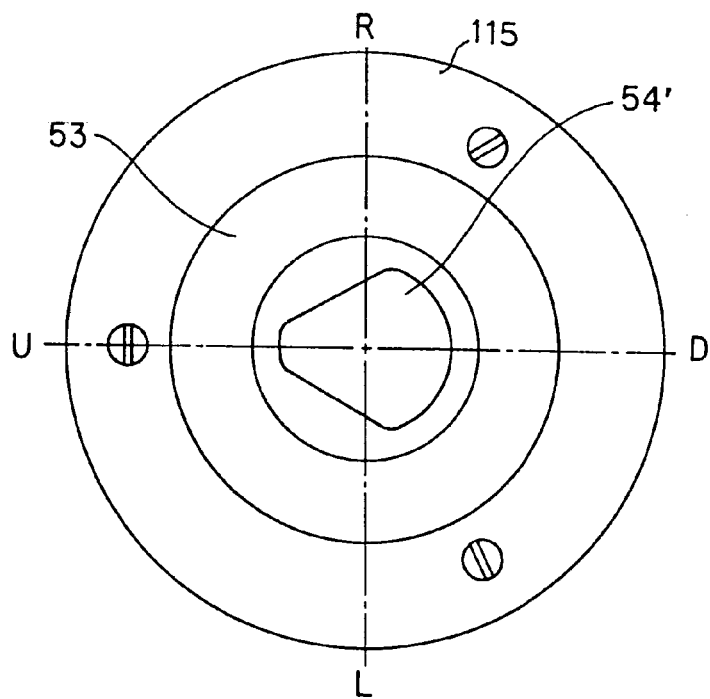
FIG. 14 is a plan view showing an operating surface of the joystick device according to a second modification of the fourth embodiment.

In the example shown in FIG. 12, the projection 112 is, for example, deviated corresponding to the upper direction of the bending instruction. The operator can know by the tactile sense the bending direction by the arranged position of the projection 112. Other structures are the same as those according to the second embodiment. Referring to FIGS. 12 to 14, up, down, left, and right directions are designated by reference symbols U, D, L, and R.

Next, the operations according to the fourth embodiment will be described.

The operator operates the endoscope while carefully viewing the monitor 8 in the electric bending endoscope. The joystick 52 can be operated in all directions at 360° and therefore the operator needs to operate the endoscope by checking the operating direction.

According to the fourth embodiment, since the projection 112 is arranged onto the operating surface 54 as the direction identifying means, the operator correctly identifies and operates the joystick device 111 in the desired bending direction by the tactile sense of the finger touched to the operating surface 54 without checking the direction by seeing the joystick device 111 positioned at hand because the deviated position of the projection 112 shows the upper direction of the bending by the joystick device 111. The operability of the electric bending endoscope is greatly improved.

FIG. 13 is a plan view showing the operating surface 54 according to a first modification of the fourth embodiment. According to the first modification, the operating surface 54 of the joystick device has a triangular planarity or V-shaped groove 113.

The groove 113 is, for example, formed to have a groove width that is narrowing from the down direction of the bending to the upper direction and therefore the upper and down directions are known by the tactile sense. Thus, the operations and advantages are substantially same as those shown in FIG. 12.

FIG. 14 is a plan view showing the operating surface 54 according to a second modification of the fourth embodiment. According to the second modification, an operating surface 54' as itself of the joystick device is not symmetrical and is deformed. The operating direction can be identified based on the deformed operating surface 54'.

Therefore, the same operations and advantages as those shown in FIG. 12 are obtained according to the second modification.

Fifth Embodiment

Figure 15:
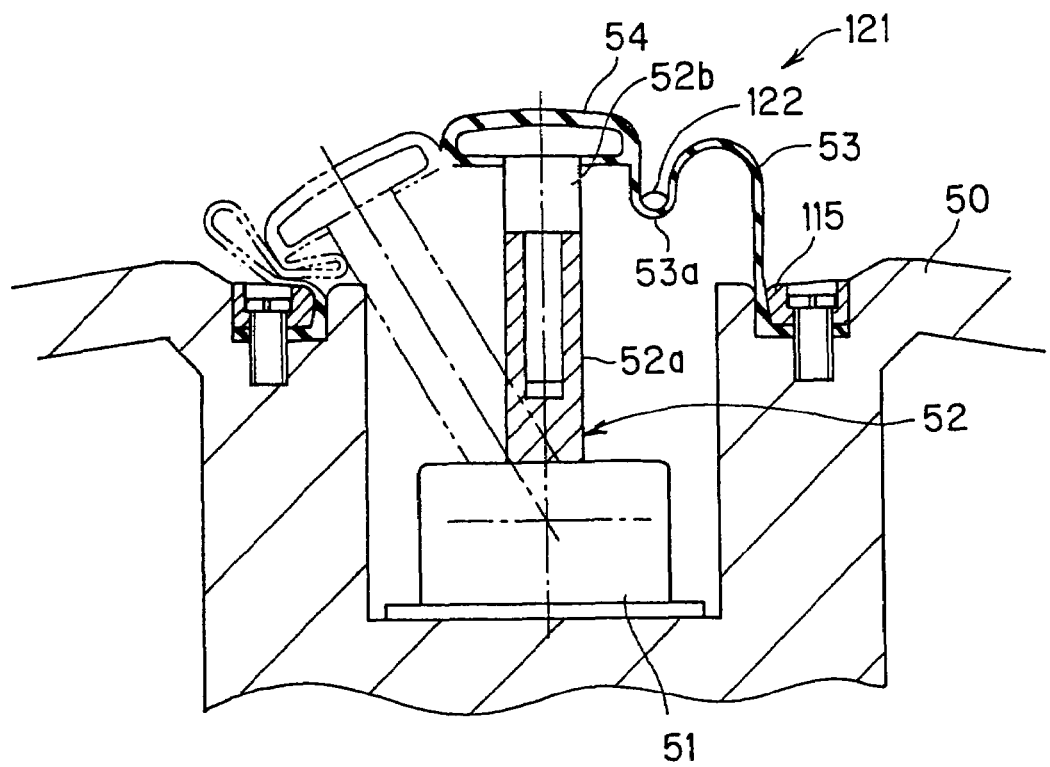
FIG. 15 is a sectional view showing the structure of a joystick device in the usual use thereof according to a fifth embodiment of the present invention.
Figure 16:
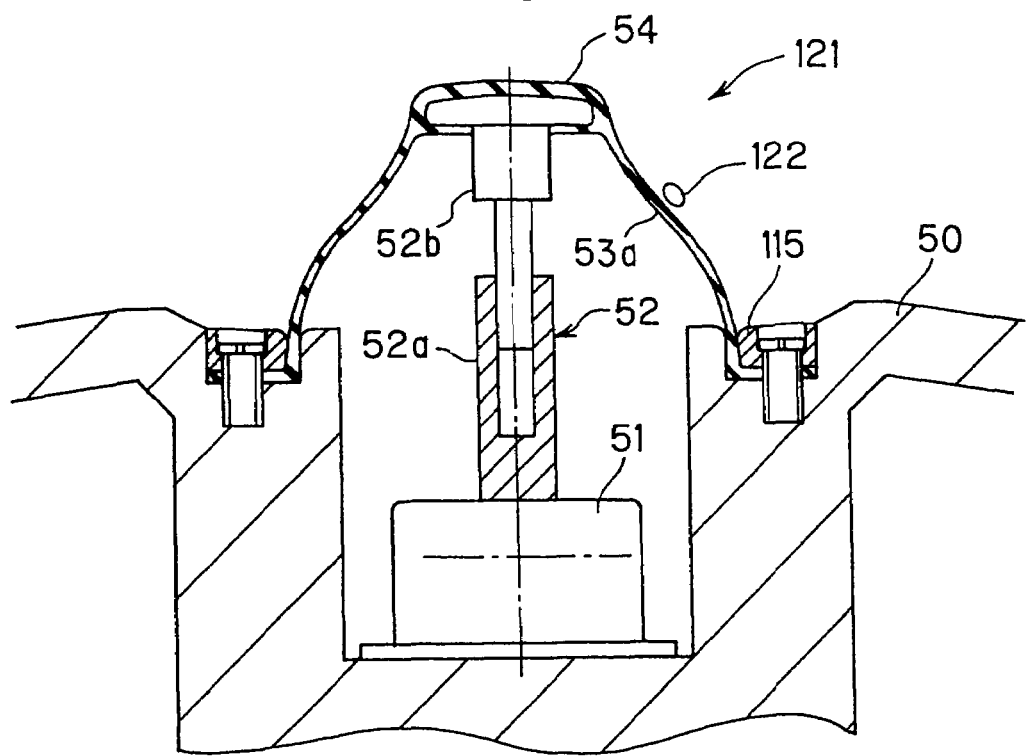
FIG. 16 is a sectional view showing a state of the joystick device in the cleaning state according to the fifth embodiment of the present invention.

Next, a fifth embodiment of the present invention will be described with reference to FIGS. 15 and 16. FIG. 15 is a sectional view showing the structure of a joystick device in the usual using state. FIG. 16 is a sectional view showing a state of the joystick device in the cleaning state.

A joystick device 121 according to the fifth embodiment shown in FIG. 15 has the structure of the joystick device, for example, according to the second embodiment, forming a bending operating device for the endoscope with the improved detergent property.

The joystick device main body 51 is fixed to a concave portion arranged to a part of the casing 50 of the operating portion, and the joystick 52 is extended from the joystick device main body 51 toward the outside of the casing 50.

The joystick 52 is connected to the joystick device main body 51 at the proximal end thereof. Further, the joystick 52 comprises two members of a hole forming member 52*a* having a hole on the down side along the central axis of the top end thereof and a sliding shaft member 52*b* which is slidably accommodated in the hole. A keycap portion arranged to the top end of the hole forming member 52*a* is integrated to the rubber cover 53 for covering it with a function of a waterproof cover, and the top surface thereof has the operating surface 54. The joystick 52 has a dimension for preventing the pulling out of a stick of the sliding shaft member 52*b* from the hole of the hole forming member 52*a* even if the rubber cover 53 is stretched in the up direction.

The rubber cover 53 has a fold portion 53*a* which is arranged like a ring around the operating surface 54 such as to smoothly incline the joystick 52, and the peripheral portion of the rubber cover 53 is fixed by a screw such that it is pressed to the casing 50 at the fixing ring 115.

Since the fold portion 53*a* is arranged in the halfway of the rubber cover 53, referring to FIG. 15, the fold portion 53*a* is folded so as to smoothly move the joystick 52 as shown by a two-dotted line upon inclining the joystick 52. However, there is a possibility that a dirt 122 such as the blood might be adhered into the fold portion 53*a* during the endoscope examination.

According to the fifth embodiment, in the cleaning time, the operating surface 54 is pulled up, the sliding shaft member 52*b* is slid, and the fold portion 53*a* of the rubber cover 53 is stretched.

That is, by sliding the sliding shaft member 52*b*, referring to FIG. 16, the fold portion 53*a* is stretched and the dirt 122 invaded to the fold portion 53*a* is easily removed.

According to the fifth embodiment, the detergent property is excessively improved with the simple structure.

Figure 17:
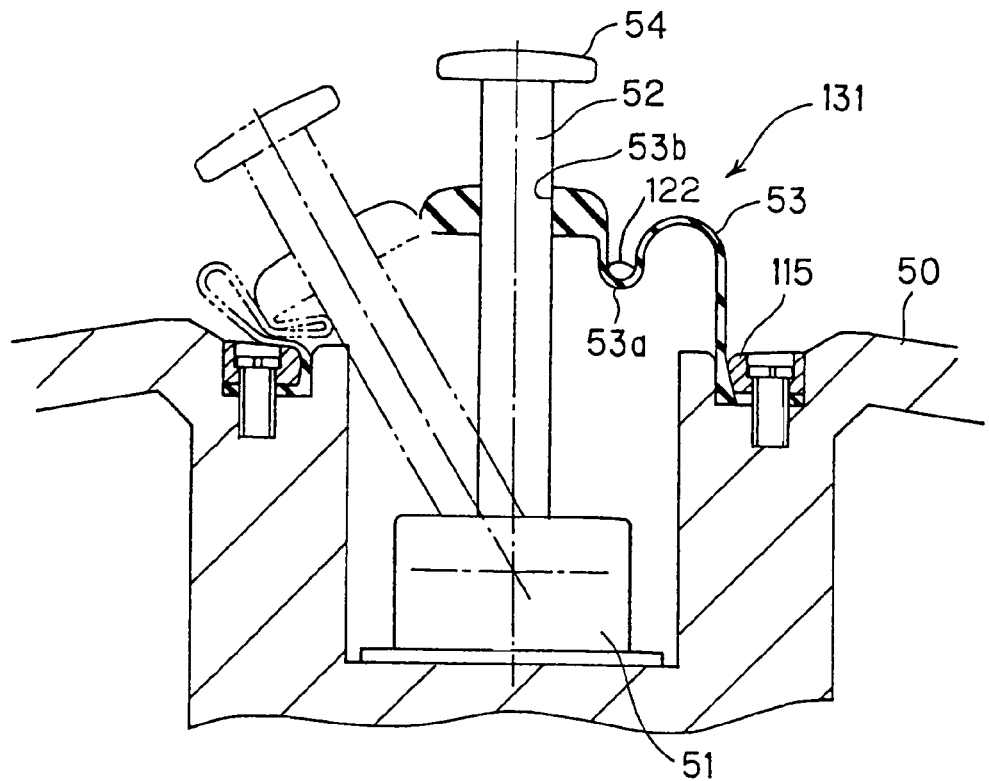
FIG. 17 is a sectional view showing the structure of the joystick device in the usual use thereof according to a modification of the fifth embodiment of the present invention.
Figure 18:
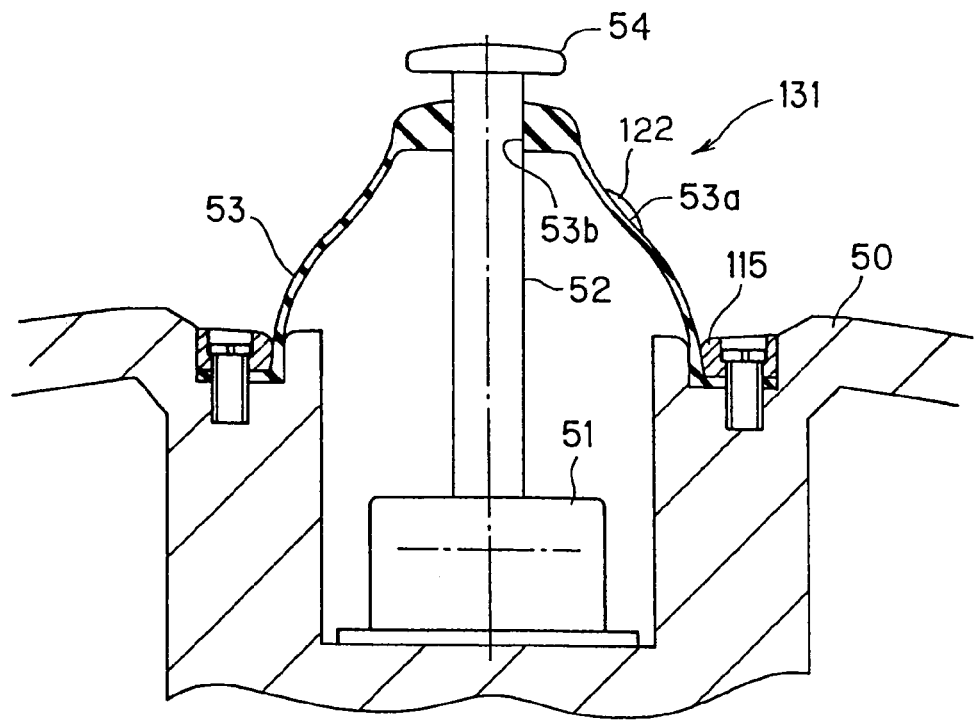
FIG. 18 is a sectional view showing the structure of the joystick device in the cleaning state according to the modification of the fifth embodiment of the present invention.

FIGS. 17 and 18 show the structure of a joystick device 131 according to a modification of the fifth embodiment. FIG. 17 is a sectional view showing the structure of the joystick device 131 in the usual using state. FIG. 18 is a sectional view showing the structure of the joystick device 131 in the cleaning state.

According to the modification, the joystick 52 shown in FIG. 15 is a solid shaft member. The top side of the joystick 52 pierces through a hole 53*b* in the center of the rubber cover 53, is projected to the outside of the rubber cover 53, and the top surface becomes the operating surface 54.

In this case, the peripheral portion through the joystick 52 pierces is thick, the rubber cover 53 is pressed in contact with the joystick 52, and the watertightness is held by the elastic force of the rubber cover 53.

In the cleaning time, the fold portion 53*a* is stretched as shown in FIG. 18 by sliding up the center portion of the rubber cover 53 along the shaft of the joystick 52 and, when the dirt is invaded, the dirt is easily removed.

The advantages according to the modification is the same as those according to the fifth embodiment shown in FIGS. 15 and 16.

As mentioned above, the electric bending endoscope according to the embodiments comprises the electric bending driving means which bends the bending portion arranged to the front end side of the inserting portion and the bending operation input means which inputs the instruction for bending the bending portion. The electric bending endoscope further comprises the bending holding means which holds the bending angle of the bending portion. Therefore, the desired bending angle is held by operating the bending angle holding means and the operability is greatly improved.

Another embodiment as the combination of the above-mentioned embodiments belongs to the present invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An electric bending endoscope comprising:
    a bending portion arranged to an inserting portion;
    a bending driving mechanism which electrically bends the bending portion;
    an operation input member for directly encoding a bending angle for instructing an operation to the bending driving mechanism so that the bending driving mechanism bends the bending portion to said encoded bending angle; and
    a bending angle holding mechanism electrically holding the bending angle of the bending portion, the bending angle holding mechanism holding the bending angle of the bending portion by way of ignoring further bending instructions from the operation input member once the bending angle holding mechanism holds the bending angle.

2. The electric bending endoscope according to claim 1, wherein the bending angle holding mechanism prevents a bending control unit for controlling the bending driving mechanism from changing control of the bending driving mechanism when an instruction for holding the bending angle of the bending portion is provided.

3. The electric bending endoscope according to claim 2, wherein the bending angle holding mechanism shuts out an instruction signal for changing the bending angle, which is inputted to the bending control unit when an instruction for holding the bending angle of the bending portion is provided.

4. The electric bending endoscope according to claim 2, wherein an input member for instructing to hold the bending angle of the bending portion is arranged to an operating portion that operates the electric bending endoscope.

5. The electric bending endoscope according to claim 2, further comprising: a notifying mechanism which notifies that the bending angle of the bending portion is held by the bending angle holding mechanism.

6. The electric bending endoscope according to claim 5, wherein the notifying mechanism displays, on a display which displays the image from the endoscope, that the bending angle is held.

7. An electric bending endoscope comprising:
    a bending portion which is arranged to an inserting portion;
    a bending control unit for bending the bending portion by electromotive power;
    an operation input member for directly encoding a bending angle for instructing an operation to the bending control unit so that the bending control unit bends the bending portion to said encoded bending angle; and
    a bending angle holding mechanism which holds the bending angle of the bending portion until an instruction for releasing the holding of the bending angle of the bending portion is provided, the bending angle holding mechanism holding the bending angle of the bending portion by way of holding the operation input member in a state of an inputted operation amount, the bending angle holding mechanism comprising a brake member formed of a solid material with a high coefficient of friction for applying frictional force to the operation input member or a member that is operated interlockingly to the operation input member, wherein the bending angle holding mechanism shuts out an instructing signal for changing the bending angle inputted to the bending control unit, when the instruction for holding the bending angle of the bending portion is provided.

8. An electric bending endoscope comprising:

a bending portion arranged to an inserting portion;

a bending driving mechanism which electrically bends the bending portion;

an inclinable joystick arranged to an operating portion and for directly encoding a bending angle for instructing an operation to the bending driving mechanism so that the bending driving mechanism bends the bending portion to said encoded bending angle;

a brake mechanism comprising a brake member which is arranged to surround the joystick, the brake member being moved in an axial direction of the joystick, the brake member holding the joystick in a state of an inputted operation amount, the brake member being formed of a solid material with a high coefficient of friction for contacting and applying frictional force to the joystick or a member that moves interlockingly to the joystick;

an engaging ring which is arranged to surround the joystick, the engaging ring being rotated to move the brake member in the axial direction of the joystick, the engaging ring holding the joystick or the member that moves interlockingly to the joystick in a state where the frictional force is applied thereto;

an engaging lever rotating the engaging ring and projected from the engaging ring;

a male screw arranged to the outer circumference of the brake mechanism; and a screw ring having a female screw to be screwed to the male screw, the screw ring variably setting a contact amount between the brake mechanism and the joystick or the member that moves interlockingly to the joystick by operating the engaging lever.

* * * * *